United States Patent [19]

Smith

[11] Patent Number: 5,243,119
[45] Date of Patent: Sep. 7, 1993

[54] ALKENE DIMERIZATION

[75] Inventor: R. Scott Smith, Baton Rouge, La.

[73] Assignee: Ethyl Corporation, Richmond, Va.

[21] Appl. No.: 619,483

[22] Filed: Nov. 29, 1990

Related U.S. Application Data

[63] Continuation of Ser. No. 472,889, Jan. 31, 1990, abandoned, which is a continuation-in-part of Ser. No. 282,674, Dec. 12, 1988, abandoned.

[51] Int. Cl.⁵ .................................................. C07C 2/10
[52] U.S. Cl. .................................. 585/516; 585/510; 585/520
[58] Field of Search ........................ 585/516, 510, 520

[56] References Cited

U.S. PATENT DOCUMENTS

| | | | |
|---|---|---|---|
| 3,185,745 | 5/1965 | Lindsay | 585/516 |
| 3,255,282 | 6/1966 | Lindsay | 585/516 |
| 4,388,480 | 6/1983 | Imai et al. | 585/516 |

FOREIGN PATENT DOCUMENTS

| | | | |
|---|---|---|---|
| 0083083 | 7/1983 | European Pat. Off. | 585/516 |
| 1078736 | 4/1986 | Japan | 585/516 |
| 1083135 | 4/1986 | Japan | 585/516 |

OTHER PUBLICATIONS

Wilkes, Proceedings of the World Petroleum Congress, vol. 5, 299–308 (1968).

Primary Examiner—Anthony McFarlane
Attorney, Agent, or Firm—Richard J. Hammond

[57] ABSTRACT

A normal 1-alkene containing 3–8 carbons is dimerized in the presence of a supported alkali metal as a catalyst and about 10–100 mol %, based on the amount of alkali metal catalyst, of an oxide of sodium, potassium, rubidium, and/or cesium as a co-catalyst. In preferred embodiments of the invention, the alkene is propene, the alkali metal is potassium or a potassium alloy, and the co-catalyst is sodium oxide.

1 Claim, No Drawings

ALKENE DIMERIZATION

CROSS-REFERENCE TO RELATED APPLICATION

This application is a continuation of application Ser. No. 472,889, filed Jan. 31, 1990, now abandoned, which is a continuation-in-part of copending application Ser. No. 282,674, filed Dec. 12, 1988, now abandoned.

FIELD OF INVENTION

This invention relates to the dimerization of alkenes and more particularly to a method of increasing the reaction rate and/or product yield in such processes which are catalyzed by alkali metals.

BACKGROUND

As disclosed in U.S. Pat. No. 3,255,272 (Lindsay), it is known that alkenes can be dimerized in the presence of supported or unsupported alkali metals as catalysts, although the patentee appears to indicate that the supported catalysts are inferior to unsupported catalysts in the reactions. Such processes are of interest for the dimerization of alkenes in general, but they are of particular interest for the dimerization of normal 1-alkenes containing 3-8 carbons, especially propene.

The dimerization of propene typically results in the formation of a mixture of hexenes, one of which is 4-methylpentene-1, a compound which is useful as a fuel additive and as a monomer which can be employed to prepare desirable homopolymers and copolymers. The more attractive propene dimerizations are those which maximize the amount of 4-methylpentene-1 formed.

Japanese Published Applications 61-78736 (Nippon Oil) and 61-83135 (Nippon Oil) teach that propene can be dimerized with high selectivity to 4-methylpentene-1 in the presence of a catalyst composition obtained by (1) heating a mixture of appropriate potassium and aluminum compounds at 400°-2000° C. for 1-20 hours to prepare a support corresponding to the formula $K_2O.x-Al_2O_3$, (2) supporting at least one of sodium, potassium, sodamide, and potassium amide thereon, (3) optionally treating the product with hydrogen and/or oxygen, and (4) finally treating the product with an ester. However, the preparation of these catalyst compositions is inconvenient.

European Patent Application 83083 (Kawamoto et al.) discloses the dimerization of propene with high selectivity to 4-methylpentene-1 in the presence of a catalyst composition obtained by dispersing metallic sodium and metallic potassium on a molded article comprising an anhydrous inorganic potassium compound and elemental carbon.

It has now been found that improved results can be obtained by heating a normal 1-alkene containing 3-8 carbons in the presence of a supported alkali metal as a catalyst and in the presence of at least one oxide of sodium, potassium, rubidium, or cesium as a co-catalyst, the catalyst composition containing about 200-1500 weight % of support and about 10-100 mol % of co-catalyst, based on the amount of alkali metal catalyst.

Alkenes which may be dimerized by the process of the invention are normal 1-alkenes containing 3-8 carbons, i.e., propene, butene-1, pentene-1, hexene-1, heptene-1, and octene-1. Propene is preferred.

As in Lindsay, the teachings of which are incorporated herein in toto by reference, the alkali metal employed as a catalyst may be lithium, sodium, potassium, rubidium, or cesium. However, it is preferably potassium or a potassium alloy, e.g., NaK. The amount used is a catalytic amount, generally about 2-10 mol %, based on the amount of alkene.

The alkali metal appropriately has its surface area increased by being finely divided or liquid as well as by being supported on any suitable support material, such as diatomaceous earth, activated charcoal, granular coke, silica, alumina, zeolite, pumice, porcelain, quartz, steel turnings, copper shot, sodium carbonate, potassium carbonate, etc.

The supported catalyst is preferably prepared by dispersing the alkali metal onto the support, which may already have the co-catalyst deposited thereon, in the absence of the alkene and any diluent.

The co-catalyst of the invention is an oxide of sodium, potassium, rubidium, and/or cesium and is preferably sodium oxide. Like the alkali metal, it is used in finely-divided form; and it may be incorporated into the reaction mixture as the oxide, or it may be generated in situ, e.g., by oxidizing the supported alkali metal catalyst when the catalyst is sodium, potassium, rubidium, or cesium. Alternatively, as in a preferred embodiment of the invention, the co-catalyst may be incorporated by adsorbing onto the catalyst support the alkali metal corresponding to the desired oxide and then oxidizing the adsorbed metal to the oxide.

The reaction is conducted by heating a mixture of the alkene, the supported catalyst, and the co-catalyst under substantially anhydrous conditions at a suitable temperature, generally about 100°-250° C., preferably about 150°-200° C., to dimerize the alkene. It may be conducted in the absence of a diluent or in the presence of an excess of the alkene as the sole diluent. However, it is usually conducted in an inert diluent, e.g., a liquid alkane, cycloalkane, or aromatic hydrocarbon, such as pentane, hexane, heptane, isooctane, cyclohexane, naphthalene, decahydronaphthalane, white oils, etc.

The process of the invention proceeds at a faster rate and/or provides higher product yields with fewer by-products than comparable processes conducted in the absence of the co-catalyst. It is advantageous as a means of preparing compounds which are useful as solvents, internal standards, polymer intermediates, etc., and is particularly advantageous as a method of preparing 4-methylpentene-1 in a predominant amount.

The extent to which the use of both the support and the co-catalyst increases the selectivity to 4-methylpentene-1 in the dimerization of propene is surprising. Comparison of experiments in which both the support and the co-catalyst were employed with experiments in which neither was used, experiments in which only the support was utilized, and experiments in which only the co-catalyst was utilized demonstrate that the support and co-catalyst act synergistically to provide an increase in selectivity that is greater than the additive effect that might have been expected from the results achieved by the use of the supports and co-catalysts separately.

The following examples are given to illustrate the invention and are not intended as a limitation thereof.

COMPARATIVE EXAMPLE A

A suitable reaction vessel was sequentially charged with 4.9 g of diatomaceous earth, 50 g of n-heptane, about 2-3 g of $C_{11}$ paraffin as an internal standard, and 1.0 g of NaK (an alloy having a K content of 78% by weight). The reactor was sealed, charged with 42 g of propene at room temperature, stirred at 750 rpm, heated to 165° C. over a period of about 12 minutes, and maintained at 165° C. for the duration of the reaction. During the reaction the stirrer was periodically stopped to allow the solids to settle; and samples were drawn, allowed to cool to room temperature, and subjected to GC analysis to determine the amounts of desired 4-methylpentene-1 (4MP1) product and 4-methylpentene-2 (4MP2), 2-methylpentene-1 (2MP1), other hexene (OHEX), and methylcyclopentane (MCP) by-products. The results of the analyses are shown below.

| Time (hr.) | Pressure (psig) | Mols × 100 | | | | |
|---|---|---|---|---|---|---|
| | | 4MP1 | 4MP2 | 2MP1 | OHEX | MCP |
| 0 | 720 | 0 | 0 | 0 | 0 | 0 |
| 1.3 | 710 | 0.01 | 0 | 0 | 0 | — |
| 2.7 | 700 | 0.41 | trace | 0.03 | 0 | — |
| 4.7 | 680 | 2.03 | trace | 0.11 | trace | — |

The preceding example shows that the reaction proceeds very sluggishly at a catalyst level of about 3 mol % when the temperature is only 165° C. and the catalyst is not deposited on a support in the absence of a diluent. The following examples demonstrate that the reaction rate can be improved by either raising the temperature or depositing the catalyst on a support in the absence of a diluent.

COMPARATIVE EXAMPLE B

Comparative Example A was essentially repeated except the reaction temperature was 185° C. instead of 165° C. and it took an additional five minutes to reach the same temperature. The analytical results are shown below.

| Time (hr.) | Pressure (psig) | Mols × 100 | | | | |
|---|---|---|---|---|---|---|
| | | 4MP1 | 4MP2 | 2MP1 | OHEX | MCP |
| 0 | 860 | 0 | 0 | 0 | 0 | 0 |
| 1 | 840 | 0.04 | 0 | 0 | 0 | — |
| 2 | 810 | 1.70 | 0 | 0.08 | 0.08 | — |
| 3 | 770 | 3.34 | trace | 0.15 | 0.15 | — |
| 5 | 670 | 6.94 | 0.50 | 0.21 | 0.21 | 0.30 |
| 7 | 540 | 11.9 | 2.10 | 0.27 | 0.27 | 0.67 |

COMPARATIVE EXAMPLE C

Comparative Example A was followed except that the sequential charge to the reaction vessel consisted of (A) the supported catalyst obtained by adding 0.85 g of NaK to 8.9 g of calcined alumina with stirring at room temperature in a dry box to provide a sky-blue powder in 10 minutes with no visual evidence of undispersed NaK, (B) 50 g of n-heptane, (C) 2.99 g of the GC standard, and (D) 46 g of propene. The analytical results are shown below.

| Time (hr.) | Pressure (psig) | Mols × 100 | | | | |
|---|---|---|---|---|---|---|
| | | 4MP1 | 4MP2 | 2MP1 | OHEX | MCP |
| 0 | 800 | 0 | 0 | 0 | 0 | 0 |
| 2 | 760 | 1.64 | 0.22 | 0.02 | 0.01 | — |
| 4 | 700 | 4.1 | 0.59 | 0.06 | 0.01 | — |
| 6 | 620 | 8.05 | 1.04 | 0.13 | 0.02 | 0.42 |

EXAMPLE I

Comparative Example B was essentially repeated except that 0.52 g of −325 mesh sodium oxide was mixed with the diatomaceous earth before it was charged to the reaction vessel. The analytical results are shown below.

| Time (hr.) | Pressure (psig) | Mols × 100 | | | | |
|---|---|---|---|---|---|---|
| | | 4MP1 | 4MP2 | 2MP1 | OHEX | MCP |
| 0 | 880 | 0 | 0 | 0 | 0 | 0 |
| 1 | 860 | 0.18 | 0 | 0.01 | 0 | — |
| 2 | 830 | 2.31 | 0.08 | 0.19 | 0 | — |
| 4 | 680 | 8.63 | 0.46 | 0.78 | 0.18 | — |
| 6 | 540 | 14.42 | 1.75 | 1.23 | 0.55 | — |
| 7 | 490 | 18.6 | 2.39 | 1.49 | 0.78 | trace |

EXAMPLE II

Comparative Example C was essentially repeated except that the initial charge to the reaction vessel was a supported catalyst/co-catalyst obtained by (1) mixing 0.5 g of freshly cut sodium with 20 g of calcined alumina (previously degassed to remove residual oxygen) in a nitrogen-filled flask in a glove box, (2) removing the flask from the glove box and heating to 130° C. under nitrogen, with stirring begun at about 100° C., (3) raising the bath temperature to 160° C. after one hour, (4) feeding 5 volume % oxygen in nitrogen for 1.5 hours, (5) cooling the resulting gray powder to 100° C. under the oxygen-nitrogen mixture, (6) allowing it to cool to room temperature under nitrogen, and (7) adding 0.85 g of NaK dropwise to 8.9 g of the thus-formed sodium oxide/alumina with stirring at room temperature in a glove box to form a gray-blue powder with no visual evidence of undispersed NaK. The analytical results are shown below.

| Time (hr.) | Pressure (psig) | Mols × 100 | | | | |
|---|---|---|---|---|---|---|
| | | 4MP1 | 4MP2 | 2MP1 | OHEX | MCP |
| 0 | 760 | 0 | 0 | 0 | 0 | 0 |
| 2 | 680 | 3.8 | 0.77 | 0.28 | 0.20 | — |
| 4 | 530 | 13.5 | 2.10 | 0.93 | 0.44 | — |
| 6 | 400 | 22.6 | 3.78 | 1.40 | 1.09 | 0 |

COMPARATIVE EXAMPLE D

Comparative Example B was essentially repeated except that no catalyst support was employed. The analytical results are shown below.

| Time (hr.) | Pressure (psig) | Mols × 100 | | | | |
|---|---|---|---|---|---|---|
| | | 4MP1 | 4MP2 | 2MP1 | OHEX | MCP |
| 0 | 870 | 0 | 0 | 0 | 0 | 0 |
| 3 | 840 | 1.3 | 0 | 0 | 0 | 0 |
| 7 | 720 | 6.7 | 1.2 | 0.5 | 0.2 | 0 |

COMPARATIVE EXAMPLE E

Comparative Example D was essentially repeated except that 0.52 g of −325 mesh sodium oxide powder was added to the NaK catalyst. The analytical results are shown below.

| Time | Pressure | Mols × 100 | | | | |
|---|---|---|---|---|---|---|
| (hr.) | (psig) | 4MP1 | 4MP2 | 2MP1 | OHEX | MCP |
| 0 | 860 | 0 | 0 | 0 | 0 | 0 |
| 3 | 700 | 7.5 | 2.3 | 0.6 | 0.6 | 0 |
| 7 | 450 | 18.1 | 8.9 | 1.0 | 3.1 | 0 |

Comparison of the product amounts formed at the stage of 20% conversion in Example I and in Comparative Examples B, D, and E shows that (A) the selectivity to 4MP1 was increased by 5.1% by using a support in the absence of sodium oxide, decreased by 12.8% by using sodium oxide in the absence of a support, and increased by 10.3% by using both the support and the sodium oxide and (B) the 4MP1/4MP2 ratio was increased by 133.3% by using a support in the absence of sodium oxide, decreased by 50% by using sodium oxide in the absence of a support, and increased by 216.7% by using both the support and the sodium oxide. The results on which these calculations were based are shown below.

| Example | 4MP1 Selectivity (%) | 4MP1/4MP2 |
|---|---|---|
| D | 78 | 6/1 |
| B | 82 | 14/1 |
| E | 68 | 3/1 |
| I | 86 | 19/1 |

It is obvious that many variations may be made in the products and processes set forth above without departing from the spirit and scope of this invention.

What is claimed is:

1. In a process for dimerizing a normal 1-alkene containing 3–8 carbons in the presence of a supported alkali metal as a catalyst, the improvement which comprises conducting the reaction in the presence of an oxide of sodium, potassium, rubidium, and/or cesium as a co-catalyst, the catalyst composition containing about 200–1500 weight % of support and about 10–100 mol % of co-catalyst, based on the amount of alkali metal catalyst.

* * * * *